Figure 1:
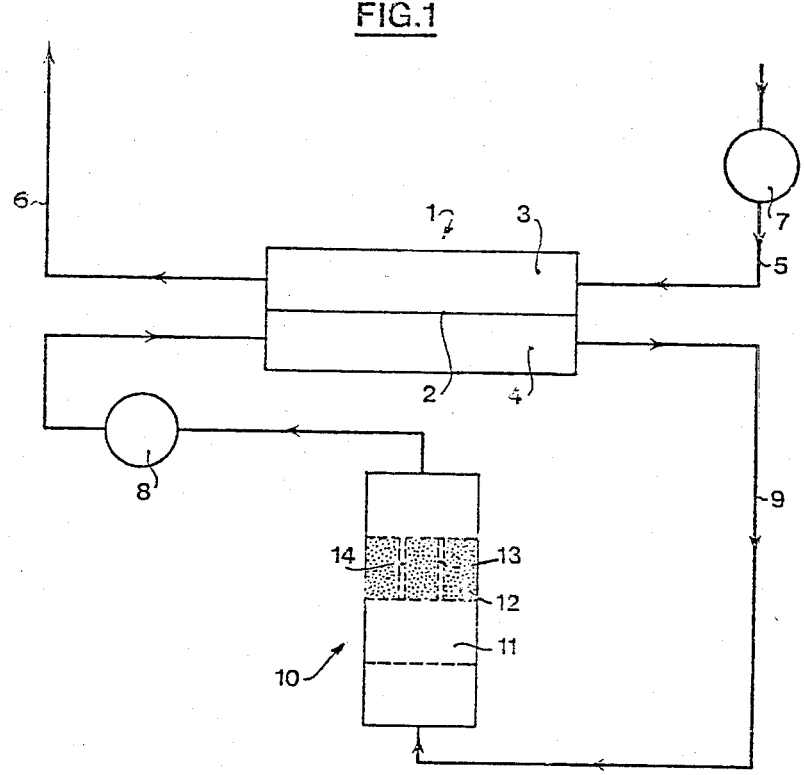

United States Patent [19]

Smakman et al.

[11] Patent Number: 4,542,015
[45] Date of Patent: Sep. 17, 1985

[54] DIALYSIS APPARATUS AND PROCESS FOR CONTROLLING THE PHOSPHATE LEVEL OF BLOOD

[75] Inventors: Robert Smakman, Nigtevecht; Gerrit H. van den Berg, Amsterdam, both of Netherlands

[73] Assignee: Organon Teknika B.V., Oss, Netherlands

[21] Appl. No.: 409,513

[22] Filed: Aug. 19, 1982

Related U.S. Application Data

[60] Continuation of Ser. No. 70,630, Aug. 29, 1979, abandoned, which is a division of Ser. No. 895,057, Apr. 10, 1978, Pat. No. 4,213,859.

[30] Foreign Application Priority Data

Apr. 12, 1977 [NL] Netherlands .......................... 7703937

[51] Int. Cl.$^4$ .......................... A61K 31/74; C08D 5/20
[52] U.S. Cl. .......................................... 424/79; 521/28
[58] Field of Search ............... 521/28, 31, 25; 424/79

[56] References Cited

U.S. PATENT DOCUMENTS

| | | | |
|---|---|---|---|
| 3,012,937 | 12/1961 | Schlichting | 424/79 |
| 3,079,428 | 2/1963 | Baer | 521/31 |
| 3,501,401 | 3/1970 | Calmon | 521/28 |
| 3,947,572 | 3/1976 | Borodkin | 424/79 |

FOREIGN PATENT DOCUMENTS 2070032 9/1981 United Kingdom ................. 521/25

*Primary Examiner*—Joseph L. Schofer
*Assistant Examiner*—Peter F. Kulkosky
*Attorney, Agent, or Firm*—Stevens, Davis, Miller & Mosher

[57] ABSTRACT

An apparatus for purifying blood has a blood compartment and a clearance compartment separated by a semipermeable membrane. The apparatus includes a device containing a cation exchange resin charged with metal ions whose phosphates are insoluble in water. Metal salts of iron, aluminum, zirconium, lanthanum, thorium and tin are deposited on a cation exchange material and the charged cation exchange resin is contacted with dialysis liquid. The process of treating blood with the dialysis liquid is also contemplated.

16 Claims, 2 Drawing Figures

DIALYSIS APPARATUS AND PROCESS FOR CONTROLLING THE PHOSPHATE LEVEL OF BLOOD

This is a continuation of application Ser. No. 70,630 filed Aug. 29, 1979, now abandoned, which in turn is a division of application Ser. No. 895,057, filed Apr. 10, 1978, now U.S. Pat. No. 4,213,859.

The invention relates to an apparatus for the purification of blood, provided with at least one selectively permeable membrane, a blood compartment on one side of the membrane and a clearance compartment on the other side thereof, through which compartments there are passed respectively the blood and a clearance liquid for removing the waste products from the blood, and a sorbent which is in contact with the clearance liquid and serves to extract phosphates from the liquid discharged from the clearance compartment.

It is known that hemodialysis may be successfully used especially in the case of chronic renal insufficiency. The blood of the patient is fed externally of the body through an artificial kidney in which harmful waste products such as urea, creatinine, uric acid, ammonium, phosphates, potassium, and the like are removed. In the artificial kidney the blood to be purified is passed over a selectively permeable membrane.

This membrane is permeable to water and to the abovementioned low-molecular waste products, but is not permeable to relatively large particles such as red and white blood corpuscles and most plasma proteins.

The composition of the clearance or dialysis liquid passing through the clearance compartment, i.e. the compartment containing the dialysis liquid, is as a rule adapted to that of normal plasma. As a result, the essential electrolytes will not have such differences in concentration as would lead to undesired diffusion of these electrolytes to the clearance compartment.

However, it is also known that instead of using a dialysis liquid, the blood may be purified by means of an ultrafilter. The latter also has a selectively permeable membrane, but in the clearance compartment the liquid originating from the plasma contains low-molecular substances which have passed through the membrane because of the application of pressure on the plasma. After this liquid has been freed from waste products, it is fed back to the blood before the latter is returned to the patient.

When use is made of a dialysis liquid, it is common practice for it to be fed to the artificial kidney at a rate of about 500 ml per minute. So, for instance, with a dialysis which lasts 8 hours, 240 liters of fresh dialysis liquid are required. The total volume can be prepared in advance and stored in a big tank (batch-tank system) or it can be continuously prepared during dialysis by diluting a liquid concentrate (concentrate dilution system). The batch-tank system has the disadvantage that it calls for the use of a tank having a capacity of as high as a few hundred liters, which is difficult to be kept sterile for a long time. The drawback to the concentrate dilution system is that it calls for an intricate apparatus in order that a proper dilution may continuously be ensured.

The amount of dialysis liquid required may be considerably reduced by employing a system using activated charcoal and ion exchangers for the regeneration or purification of the dialysis liquid after it has passed through the artificial kidney and before it is fed back to the artificial kidney. Such a regeneration system is known from, for instance, the Netherlands Patent Application No. 7,009,608. In the described regeneration, urea is converted into ammonium carbonate by means of urease, after which the ammonium ions are attached to a zirconium phosphate cation exchanger. The spent dialysis liquid is subsequently passed over hydrated zirconium oxide which absorbs phosphates from it.

Organic waste products such as uric acid and creatinine, are removed from the dialysis liquid with the aid of active carbon. Thus, only a few liters of dialysis liquid will suffice for carrying out a dialysis treatment.

In another well-known artificial kidney described in U.S. Pat. No. 3,617,545 the dialysis liquid is purified by electrodialysis. The dialysis liquid coming from the artificial kidney is demineralized in an electrodialyser and subsequently passed through a column of urease for converting urea into ammonium bicarbonate. Next, the dialysis liquid flows to a cation exchanger which retains the ammonium, and thereafter back to the electrodialyser for recovering the ions lost in the initial passage, and subsequently through a column of active carbon for the removal of uric acid and creatinine and finally cleared of phosphates and sulphates by an anion exchanger (Amberlite IRA 400 or Permutit S1)before being passed back to the clearance compartment of the artificial kidney.

There has been no satisfactory method so far for the removal of phosphates from the dialysis liquid which usually occur in it in the form of $HPO_4^{2-}$ and $H_2PO_4^-$.

There are several disadvantages to the use of inorganic ion exchangers for that purpose. Hydrated or non-hydrated aluminium oxide, for instance, displays a toxic side effect; a satisfactorily reproducible preparation of hydrated zirconium oxide is found to give quite some problems; and the phosphate-retaining capacity of hydrated iron oxide rapidly deteriorates with time.

Organic anion exchangers are incapable of removing phosphate sufficiently because of the high excess of chloride ions over the phosphate ions in the dialysis liquid.

For instance, strongly basic anion exchangers in this medium will take up as little phosphate ($HPO_4^{--}$) as about 10 meq per liter of ion exchanger.

There has now been found a specific sorbent which has a high capacity, rapidly removes phosphate, and has satisfactorily reproducible properties.

The apparatus according to the invention is characterized in that the sorbent used is an organic cation exchange material which is charged with ions of a metal whose phosphate is poorly soluble in water.

It should be noted that methods for the removal of phosphate from liquids with the aid of sorbents are in themselves known to be used for the purification of sea and waste water. For instance the journal Okeanologya, 13 (1973) 2 and the PB report 203 069 (1970) of the U.S. Nat. Tech. Inform. Service contain descriptions of methods for the removal of phosphates from sea or waste water using strongly acid cation exchangers charged with/-iron(III)-ions. The technique of the purification of sea water or waste water, however, is totally different from that employed for the purification of blood, in which case also medical requirements are to be considered.

In order that the sorbent may be medically permissible and capable of a rapid and high take up of phosphate it should be formed preferably by an organic cation exchanger charged with iron ions. A particularly suitable sorbent is a cation exchanger charged with iron (III) ions. If as sorbent instead of a cation exchanger charged with iron (III) ions there is used a cation exchanger charged with ions of metals whose phosphates are also insoluble, such as ions of metals selected from the group of thorium, tin, lanthanum, aluminum and zirconium, then it should of course be ensured that possible toxic effects as a result of the metal ions are effectively controlled. By poorly soluble phosphates are to be understood here phosphates having a solubility not higher than 10 mg/l in water.

The cationic exchange resin may be charged with metal ions in any suitable manner. To this end the cation exchanger may be in a suitable form such as the $H^+$ form or entirely or partly in a salt form, for instance the $Na^+$ form. Charging is effected in a known manner, for instance by means of an aqueous solution of a salt of the particular metal used. The charging temperature may vary between wide limits, for instance between 0° and 100° C. The charging time is generally in the range of a few minutes to 10 hours.

Use may be made to advantage of a cation exchanger having weakly acid groups, because they give rise to only a low concentration in the effluent of the metal ions with which it is charged (metal leakage). As examples of suitable weakly acidic groups may be mentioned carboxylic acid groups, phosphonic acid groups and/or amidoxime groups. In particular, the cation exchanger may contain aminocarboxylic acid groups and/or iminodicarboxylic acid groups, for instance those in which the carboxylic acid group contains 1 to 5 carbon atoms, more particularly aminoacetic acid groups and/or iminodiacetic acid groups. It is especially the last-mentioned type which displays a remarkably low metal leakage.

Despite the advantage of a low metal leakage when use is made of cation exchangers having weakly acid groups, the present invention is not at all limited to devices using this type of cation exchanger. From the point of view of phosphate-retaining power the cation exchangers that contain strongly acid groups are also very suitable. Moreover, the sorbents prepared therefrom will generally take up considerable amounts of potassium in addition to phosphates, which is of interest since potassium is as a rule present in too high concentrations in the blood of kidney patients. Particularly suitable for a combined take up of phosphate ions and potassium ions are cation exchangers containing sulphonic acid groups.

Organic cation exchangers are known in themselves and may be prepared in any suitable manner. A weakly acid cation exchange resin containing carboxylic acid groups may be obtained for instance by hydrolysis of a copolymer of a nitrile or a (meth)acrylic ester or by copolymerization of (meth)acrylic acid.

A weakly acid cation exchanger with phosphonic acid groups may be prepared for instance by phosphorylation of a matrix followed by oxidation or, for instance, by reaction of a haloalkylated matrix with phosphorus trichloride, followed by hydrolysis of the reaction product.

A weakly acid cation exchanger containing aminocarboxylic acid groups and/or iminodicarboxylic acid groups may for instance be prepared by haloalkylation of a matrix, followed by reaction with an aminocarboxylic acid or an iminodicarboxylic acid having 1 to 5 carbon atoms per carboxylic acid group or by preference a derivative thereof such as a nitrile or an ester, in which latter case the reaction product is subjected to hydrolysis.

This cation exchanger also may be prepared by bringing a halocarboxylic acid having 1 to 5 carbon atoms or a derivative thereof into reaction with a haloalkylated and subsequently aminated matrix. Amination may be carried out by means of, for instance, ammonia, ethylene diamine or polyamines, for instance: tetraethylene pentamine.

A cation exchanger having amidoxime groups may for instance be obtained by bringing a copolymer having nitrile groups into reaction with hydroxylamine.

A strongly acid cation exchanger having sulphonic acid groups can be prepared in a known manner by, for instance, sulphonation of a matrix with, for instance, sulphuric acid or chlorosulphonic acid or by reaction of a matrix with sulphur chloride followed by oxidation, as disclosed in British Patent Specification No. 1,270,127. Optionally, the strongly acid cation exchangers having aromatic nuclei may further be treated with, e.g. oleum.

The chemical composition of the matrix or the basic polymer of the cation exchanger also may vary. However, it preferably consists of a polymer or a polycondensation product of an aromatic compound and/or a (meth)acryl or vinyl compound, for which with advantage use may be made of a phenol-formaldehyde resin or a copolymer of a vinyl aromatic compound and/or an acryl or vinyl compound. For the preparation of the phenol-formaldehyde resin not only basic phenol itself, but also other phenols, for instance cresols or diphenylol propane may be used.

In the preparation of the polymer from a vinylaromatic compound use may be made of monovinyl aromatic compounds such as styrene, vinyl toluene, vinyl ethyl benzene, vinyl naphthalene or vinyl anisole, or mixtures of the afore-mentioned compounds.

It is preferred that use should be made of styrene. Besides (a)monovinyl aromatic compound(s) there may be employed one or more acryl compounds, for instance: acrylonitrile or methacrylonitrile, and/or acrylic or methacrylic esters. In the preparation of weakly acid cation exchangers preference is given to the use of acryl compounds. The preparation of the matrix also may be carried out in the presence during polymerization of a cross-linking monomer, for instance in an amount not higher than 80% by weight, calculated on the total amount of monomers, which step is not required, however, if the polymer is as yet cross-linked after polymerization, for instance in the haloalkylation or by electromagnetic radiation or accelerated electrons. As cross-linking monomer there is used a compound having at least two ethylenically unsaturated groups, for instance, 1,3-butadiene, isoprene or vinyl methacrylate, but preferably di- or polyvinyl aromatic compounds, such as divinyl ethyl benzene, trivinyl benzene and more particularly technical divinyl benzene (60% by weight of divinyl benzene and 40% by weight of ethyl styrene).

The basic polymer may be prepared in any suitable manner, for instance by suspension polymerization of one or more monomers at a temperature generally in the range of 10° to 160° C. in the presence of a radical initiator, for instance benzoyl peroxide, lauroyl peroxide, cumene hydroperoxide and/or azobisisobutyronitrile.

It is preferred that the matrix of the cation exchanger should be macroporous, since in that case a very high and rapid phosphate sorption is obtained. To this end the polymerization may be carried out, if required, in the presence of one or more compounds which can precipitate and/or solvate the polymer to be prepared, for instance: hexane, heptane, cyclohexane, amyl alcohol, cyclohexanol, benzene, toluene and/or chlorobenzene. Alternatively, a linear polymer, such as polystyrene, may be dissolved in the monomeric compound(s) and be extracted after polymerization.

The use of a strongly acid cation exchanger with a high degree of cross-linking of the macroporous matrix is of advantage because such a sorbent shows a high selectivity to potassium ions as well as high and rapid phosphate take up. By a matrix having a high degree of cross-linking is to be understood here a matrix containing at least 10% by weight of a cross-linked monomer.

A much preferred embodiment of the apparatus according to the invention is characterized in that the sorbent is also charged with alkaline earth metals, more particularly calcium ions and/or magnesium ions. In this way the sorption of these ions from the dialysis liquid can be controlled in order that the correct Ca- and Mg levels in the blood may be maintained without there being any need for external replenishment of these alkaline earth metals.

In another embodiment of the apparatus provided by the invention the sorbent is included in capsules having a cationic semi-permeable wall. Such an embodiment may be of advantage in the case where the sorbent might give off substances that must not enter the blood. It is also possible for the sorbent according to the invention to be used in direct contact with the blood, i.e. without engaging a dialysis circuit. In that case it is preferred that the sorbent should be included in a capsule whose wall is compatible with the blood; a suitable material for this purpose is, for instance, cellulose acetate.

The sorbent may be brought into a reservoir, for instance, a cartridge or a column, after which the phosphate containing liquid is passed through the reservoir in the usual manner. In a different embodiment according to the invention the sorbent is contained in the clearance compartment of the artificial kidney.

After the sorbent has taken up sufficient phosphate, it may optionally be regenerated, for instance with iron (III) chloride in the case of an iron-charged cation exchanger. If in the regeneration also the metal is removed, then the cation exchanger can be re-charged with this or some other metal.

In the dialysis care should further be taken that the patient does not develop acidosis. Prevention thereof may be effected by giving the patient a dose of bicarbonate ions. General practice is that for the duration of the dialysis an aqueous solution of sodium acetate is added to the dialysis liquid, advantage being taken of the fact that the acetate ions pass through the usually employed dialysis membranes and are converted into bicarbonate ions in the patient. Administering sodium acetate, however, calls for a series of operations and the use of intricate control apparatus. Moreover, it causes an undesirable increase in the sodium ion concentration in the blood.

The invention also provides an apparatus for adding in a simple and reliable manner the desired amount of bicarbonate ions and/or acetate ions at the required speed. To this end use is made of a basic anion exchanger which is at least partly charged with bicarbonate ions and/or acetate ions and exchanges these for chloride ions of the dialysis liquid. It is preferred that the ion exchanger should be strongly basic. The amount of dialysis liquid per unit time coming into contact with the anion exchanger is determinative of the rate at which acetate ions and/or bicarbonate ions are released. The total amount required can be set with the amount of anion exchanger. It should be added that the organic anion exchanger which is at least partly charged with acetate ions and/or bicarbonate ions also may be used in combination with sorbents and/or ion exchangers other than the ones according to the invention.

The invention further relates to a method of preparing a cation exchanger charged with metal ions. It is characterized in that before or after the cation exchanger is charged with the metal ions, it is charged with from 10% to 100% alkali metal ions. A weakly acid cation exchanger with carboxyl groups is preferably charged with at least 80%, and it is preferred that a weakly acid cation exchanger with iminodicarboxylic acid groups should be charged with 40–60% by weight alkali metal ions.

Sodium ions are particularly suitable. An alkali metal charge is particularly of importance for strongly acid cation exchangers in order to inhibit metal leakage and/or a decrease in pH value during dialysis. To this end and to increase the phosphate retaining power it is also of importance that the pH value during and/or after charging with the metal ions is set to an appropriate value.

The invention further relates to a method for the preparation of substances for decreasing the potassium and/or the phosphate level in the blood. It is characterized in that as sorbent an organic cation exchanger charged with metals selected from the group comprising thorium, iron, tin, lanthanum, aluminum and zirconium is brought into a form suitable for oral administration.

The invention also comprises the shaped articles suitable for oral administration made by the process according to the present invention. The sorbent may for instance be contained in capsules at least one of the walls of which dissolve in the intestinal canal, so that the sorbent can take up phosphate there.

It is apparent that in that case the sorbent must not be toxic. Moreover, in the case of oral administration the sorbent may be contained in capsules having a cationic semi-permeable wall. This may be of importance if a direct contact of the solvent with its environment should be avoided.

FIG. 1 is a schematic representation of a hemodialyser. An artificial kidney 1 which has two compartments 3 and 4 separated by a selectively permeable membrane 2, i.e. a blood compartment 3 and a clearance or dialysis compartment 4. The membrane may be in any desirable form, for instance in that of flat or tubular film, or it may be a large number of hollow fibers. The blood compartment 3 is connected to the circulatory system of a patient by means of blood tubes 5 and 6. If necessary, the extracorporal transport of the blood may be assisted by a blood pump 7. Dialysis liquid flows through compartment 4 and circulates through a dialysis circuit 9 by means of a dialysate pump 8.

In the dialysis circuit 9 there is a regeneration device 10 which purifies the dialysis liquid from the waste products it has taken up from the blood in compartment 4. The regeneration device may consist of several parts connected in series or in parallel, which each serve to eliminate one or more waste products. One of these parts is a column 11 containing the sorbent provided by the invention for the removal of phosphates from the dialysis liquid. If required, the sorbents may be mixed in a particularly desired ratio and be contained in one column. After the dialysis liquid has passed through the column 11, it goes through a column 12 containing active carbon for the removal of uric acid and creatinine from the dialysis liquid. In the active carbon of column 12 there is placed a tube 13 containing a basic anion exchanger which is at least partly charged with a material containing acetate ions and/or bicarbonate ions.

This tube serves to keep the acetate and the bicarbonate content of the dialysis liquid at the desired level. However, it is also possible for the active carbon of column 12 to hold two tubes which respectively contain acetate charged and bicarbonate charged basic anion exchangers. The tube 13 is so dimensioned and constructed that only a particular part of the total stream of dialysis liquid flows through it, so that an adjustable release of acetate and bicarbonate may be obtained. It is also possible for the tube to be placed in a column packed with a different material or to be placed in a separate by-pass line through which there flows only part of the dialysis liquid.

PREPARATION OF IMINODIACETIC ACID CATION EXCHANGER

A macroporous copolymer consisting of 86% by weight of styrene and 14% by weight of technical divinyl benzene was chloromethylated in dichloroethane with monochloromethyl ether in the presence of aluminium chloride as catalyst. One part by weight of the product was brought into reaction with 2 parts by weight of diethyl ester of aminodiacetic acid dissolved in toluene. The resulting product was hydrolysed, after which the nitrogen content of the dry cation exchanger obtained was 5% by weight (calculated on dry weight).

PREPARATION OF SORBENTS I—III

From the above-described iminodiacetic acid cation exchanger the following three sorbents were prepared.

I After 300 ml of the cation exchanger had been brought into the acid form by means of 2N $H_2SO_4$ it was stirred for one hour in the presence of 300 ml of an $FeCl_3$ solution in a concentration of 2 eq/liter, and subsequently washed with soft water. The charge was then 950 meq Fe (III)/liter cation exchanger.

II After 300 ml of the cationic exchanger had been brought into the 50% $Na^+$ form using 2N NaOH, it was stirred for 1 hour in the presence of 300 ml of an Fe $Cl_3$ solution in a concentration of 2 eq/liter. Subsequently, the pH was brought to a value of 5.0 with an aqueous Na $HCO_3$ solution. Next, the cation exchanger was stirred for one hour and washed with soft water. The charge was then 1670 meq Fe (III)/liter cation exchanger.

III The cation exchanger which had been brought to about 50% of the $Na^+$ form in accordance with Example II was charged with Fe (III) with one part by volume of Fe $Cl_3$ solution (2 eq/liter) and washed with soft water. Subsequently 2 parts by volume of a solution of $CaCl_2$ (1000 meq/liter and Mg $Cl_2$ (350 meq/liter) were added to it, followed by stirring for one hour, the pH being kept at a value of 5 by means of sodium bicarbonate. After washing for a short time the Fe (III) charge was 1650 meq/l cation exchanger.

PREPARATION OF SULPHONIC ACID CATION EXCHANGER

One part by weight of macroporous copolymer of 70% by weight of styrene and 30% by weight of technical divinyl benzene was sulphonated by heating it with 8 parts by weight of 98% $H_2 SO_4$ for 2 hours at 75° C. and subsequently for 4 hours at 100° C. After slow dilution and washing with water the product (A) obtained had a capacity of 1850 meq/l.

A part of the macroporous cation exchanger A obtained was aftertreated by adding over a period of 30 minutes 1 part by weight of sodium sulphate and 10 parts by weight of oleum containing 65% by weight of sulphur trioxide per 1 part by weight of the cation exchanger.

The mixture was heated for 4 hours at a temperature of 110° C. Subsequently it was slowly diluted and washed with water. The product (B) obtained had a capacity of 2270 meq/l.

In order to prepare a sulphonic acid cation exchanger by activation with sulphur chloride, followed by oxidation 1 part by weight of the macroporous copolymer described above was left to swell in 2 parts by weight of $S_2Cl_2$. The swollen beads were cooled to $-15°$ C., and 2 parts by weight of liquid $SO_2$ were added. Then, over 1 hour, 2 parts by weight of $ClSO_3H$ were added, the reaction mixture being maintained at $-15°$ C. by cooling. The temperature of the reaction mixture was next allowed to increase slowly and finally it was heated for 12 hours at 60° C. The beads were washed with carbon disulphide and subjected to a suction action until they were air-dry. The polymer sulphide and/or polysulphide thus obtained was first oxidized for 1 hour with 30% by weight nitric acid at a temperature of between 30° and 50° C., and then oxidized by heating for 40 minutes with 60% by weight nitric acid at 90° C. After cooling, the product was washed with water. Four parts by volume of a copolymer C containing $SO_3H$ groups were obtained (per part by weight of copolymer starting material) and having a capacity of 2255 meq/l.

PREPARATION OF SORBENTS IV—XI

From the above-described non-aftertreated sulphonic acid cation exchanger A the sorbents IV - IX were prepared.

IV 300 ml of the cation exchanger together with 300 ml of a $FeCl_3$ solution in a concentration of 2 eq/liter were stirred for one hour at 25° C., followed by washing with soft water. The charge was then 1600 meq Fe (III)/liter cation exchanger.

V Example IV was repeated, with the exception that after the cation exchanger had been brought into contact with the $FeCl_3$ solution, the pH was raised to a value of 5.5 by means of an $NaHCO_3$ solution followed by stirring for one hour. After washing with soft water the charge was 1720 meq Fe (III)/liter cation exchanger.

VI After 300 ml of the cation exchanger had been brought into the $Na^+$ form until acid-free by percolation with an excess of 6% NaCl solution, it was contacted for one hour at 25° C. with 300 ml of an $FeCl_3$ solution in a concentration of 2 eq/liter, and washed with soft water. The charge was then 1650 meq Fe (III)/liter cation exchanger.

VII Example VI was repeated in such a way that subsequent to the washing treatment 1 part by volume of cation exchanger was after-washed with 3 parts by volume of aqueous 1% $NaHCO_3$ solution and washed with soft water. The charge was then 1645 meq Fe (III)/liter of cation exchanger.

VIII One part by volume of the sorbent obtained according to Example VI was charged with $Ca^{++}$ and $Mg^{++}$ by stirring the sorbent for 30 minutes in the presence of one part by volume of a solution of $CaCl_2$ (1000 meq/liter) and $MgCl_2$ (250 meq/liter). After the sorbent had been washed with soft water, it was after-washed with one part by volume of an aqueous 0.1% $NaHCO_3$ solution and again washed with soft water. The sorbent then took up very little $Ca^{++}$ and $Mg^{++}$ from the dialysis liquid. The iron charge was 850 meq/liter cation exchanger.

IX After 1500 ml of the cation exchanger had been brought into the $Na^+$ form by percolation with an excess of aqueous 6% NaCl solution, it was stirred for one hour in the presence of 1500 ml of aqueous $FeCl_3$ solution having a concentration of 200 meq/liter. After the sorbent had been washed with soft water it was charged with $Ca^{++}$ and $Mg^{++}$ with stirring for one hour in the presence of 1500 ml of an aqueous solution of $CaCl_2$ (1300 meq/liter) and $MgCl_2$ (140 meq/liter). After it had been washed with soft water it was after-washed with 1500 ml of a 0.1% $NaHCO_3$ aqueous and again washed with soft water. The iron charge was then 150 meq/liter cation exchanger.

Sorbent X was prepared according to Example IX, with the exception, however, that use was made of the pre-treated cation exchanger B, in an amount of 1000 ml. The solution of the alkaline earth metal salts had a $CaCl_2$ concentration of 1200 meq/liter. The sorbent obtained had an iron charge of 180 meq/liter cation exchanger.

Sorbent XI was prepared according to Example IX, with the exception, however, that use was made of the sulphonic acid cation exchanger C in an amount of 1000 ml. The solution of the alkaline earth metal salts had a $MgCl_2$ concentration of 160 meq/liter. The sorbent obtained had an iron charge of 190 meq/liter exchanger.

PREPARATION OF CARBONIC ACID CATION EXCHANGER

A macroporous, carbonic acid cation exchanger was prepared by hydrolysis of a macroporous copolymer of 40% by weight of ethyl acrylate, 44% by weight of acrylonitrile and 16% by weight of technical divinyl benzene. The weakly acid capacity was 2300 meq per liter of cation exchanger.

XII After 300 ml of the cation exchanger had been brought entirely into the $Na^+$ form by means of aqueous 2N NaOH it was contacted for one hour at 25° C. with 300 ml of an aqueous $FeCl_3$ solution having a concentration of 3 eq/liter. The pH was then brought to a value of 6 by means of an aqueous NaOH solution and stirring was continued for one hour. Subsequently, the cation exchanger was washed with soft water. The charge was then 2175 meq Fe (III) per liter of cation exchanger.

Figure 2:
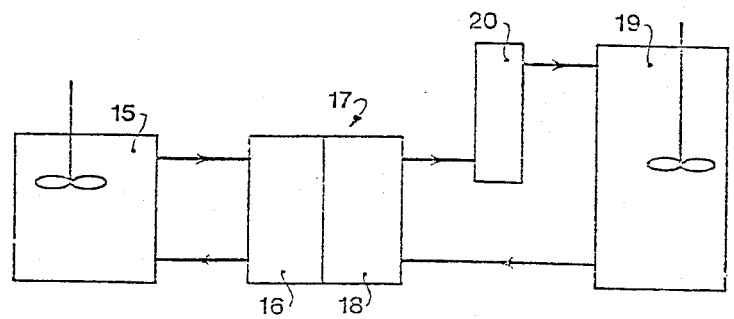

With the experimental set up illustrated in FIG. 2 the above-described sorbents were tested in vitro. In FIG. 2 a vessel 15 charged with 34 liters of a model aqueous liquid having the starting composition* mentioned in Table 1.

*The starting pH of the two liquids was set to 7.4 by means of some hydrochloric acid. From the start of the experiment 184 meq phosphate (as $HPO_4^{2-}$) were fed to the model liquid over a period of 30 minutes; in this way no precipitate was formed in the model liquid.

TABLE 1

|  | Model liquid | Dialysis liquid |
|---|---|---|
| $Na^+$ | 139.5 meq/l | 139.5 meq/l |
| $K^+$ | 3.0 meq/l | 3.0 meq/l |
| $Ca^{++}$ | 3.5 meq/l | 3.5 meq/l |
| $Mg^{++}$ | 1.0 meq/l | 1.0 meq/l |
| $Cl^-$ | 107.0 meq/l | 107.0 meq/l |
| Acetate | 15.0 meq/l | 25.0 meq/l |
| Bicarbonate | 25.0 meq/l | 15.0 meq/l |
| Phosphate (as $HPO_4^{--}$) | 0 meq/l | 0 meq/l |
| Urea | 1.0 g/l | 0 g/l |
| Creatinine | 0.1 g/l | 0 g/l |

In Examples IX-XI the model liquid contained 6.44 meq $K^+$/liter instead of 3 meq $K^+$/liter. The potassium concentration in the dialysis liquid was then 0 meq $K^+$/l instead of 3 meq $K^+$/liter.

The model liquid, the components of which occur in corresponding concentrations in the human blood, circulated through the blood compartment 16 of a dialyser 17 at a rate of 200 ml/min. The dialyser had a semipermeable membrane of cupramonium cellulose film, known under the trade name Cuprophan. The membrane had a thickness of 18 μm and a surface area of 1.3m². A dialysis liquid supplied from a 6-liter buffer vessel 19 circulated through the clearance compartment 18 at a rate of 500 ml/minute. The dialysis liquid was of the composition given in Table 1. After the dialysis liquid had left the clearance compartment 18, it passed through a column 20, containing a sorbent according to the invention. The vessels 15 and 19 were kept at a temperature of 37° C. The phosphate concentration and the acidity of the liquid in the vessel 15 were measured as a function of time and the amount of phosphate taken up by the sorbent expressed as milliequivalents was calculated. Moreover, the calcium, magnesium and iron concentrations in the vessel 15 were measured. The experiments were carried out with the sorbents I through XII in amounts of 300 ml each, except for the sorbents IX—XI, which were used in amounts of 1100 ml, 750 ml and 750 ml, respectively. In the following Table 2 are listed the phosphate, calcium, magnesium and iron ions concentrations of the model liquid in the vessel 15 measured after 360 minutes. It also gives the lowest pH values observed in the vessel 15 and the total amounts of phosphate taken up by the sorbent, which are also given per liter of sorbent.

The difference in the rate of removal of phosphate in the above-mentioned experiments were only small.

TABLE 2

| Sorbent | Meq $HPO_4^{2-}$ taken up by sorbent | Meq $HPO_4^{2-}$ taken up per liter of sorbent | Model liquid | | | | |
|---|---|---|---|---|---|---|---|
|  |  |  | Meq $HPO_4^{2-}$/l | Meq $Ca^{2+}$/l | Meq $Mg^{2+}$/l | ppm Fe | pH min. |
| I | 39 | 130 | 3.62 | 0.7 | 0.5 | <0.1 | 6.9 |

TABLE 2-continued

| Sorbent | Meq HPO$_4^{2-}$ taken up by sorbent | Meq HPO$_4^{2-}$ taken up per liter of sorbent | Model liquid Meq HPO$_4^{2-}$/l | Meq Ca$^{2+}$/l | Meq Mg$^{2+}$/l | ppm Fe | pH min. |
|---|---|---|---|---|---|---|---|
| II | 83 | 276 | 2.53 | 0.8 | 0.6 | <0.1 | 7.2 |
| III | 78 | 261 | 2.64 | 3.0 | 0.9 | <0.1 | 7.2 |
| IV | 90 | 299 | 2.36 | 1.7 | 0.9 | 1.5 | 6.7 |
| V | 76 | 253 | 2.70 | 1.8 | 0.9 | 0.5 | 7.4 |
| VI | 99 | 329 | 2.12 | 1.7 | 0.9 | 0.7 | 7.5 |
| VII | 71 | 236 | 2.83 | 1.6 | 0.9 | <0.1 | 7.4 |
| VIII | 83 | 276 | 2.53 | 3.4 | 1.0 | <0.1 | 7.4 |
| IX | 99 | 90 | 2.13 | 3.3 | 1.0 | <0.1 | 7.4 |
| X | 90 | 120 | 2.35 | 3.5 | 0.9 | <0.1 | 7.4 |
| XI | 100 | 133 | 2.09 | 3.3 | 1.0 | <0.1 | 7.4 |
| XII | 69 | 231 | 2.87 | — | — | <0.1 | 7.2 |

To find out the influence of cation exchangers charged with metal ions other than Fe$^{+++}$ additional experiments were carried out with the above-described iminodiacetic acid cation exchanger charged with ions of one of the metals of the group of aluminium, zirconium, lanthanum, thorium and tin.

In each experiment, 50% of the cation exchanger was brought into the Na$^+$-form by means of 2N NaOH. This was followed by washing with soft water. Subsequently, the cation exchanger was stirred for 3 hours in the presence of a solution of a salt of one of the above-mentioned metals of the group of aluminium, zirconium, lanthanum, thorium and tin.

In all cases the metal salt solution contained 3300 meq of the metal salt per liter of the starting cation exchanger. As metal salts were used AlCl$_3$.6H$_2$O, ZrOCl$_2$.8H$_2$O, LaCl$_3$.H$_2$O, Th(NO$_3$)$_4$.4H$_2$O and SnCl$_4$.5H$_2$O.

The results of the measurements after a dialysis lasting 360 minutes are listed in the following Table 3.

TABLE 3

| Metal | Meq HPO$_4^{2-}$ per liter of dialysis liquid | Meq HPO$_4^{2-}$ taken up by sorbent | Meq HPO$_4^{2-}$ taken up per liter of sorbent |
|---|---|---|---|
| Al | 2.92 | 67 | 224 |
| Zr | 3.28 | 53 | 176 |
| La | 2.91 | 68 | 225 |
| Th | 2.07 | 101 | 337 |
| Sn | 4.20 | 16 | 53 |

Unless otherwise indicated all "liquids" and solutions used herein are water or aqueous solutions. Also unless otherwise stated, all parts and percentages are by weight.

WHAT IS CLAIMED IS:

1. In a method for the preparation of a cation exchanger charged with metal ions adapted for controlling the phosphate level in blood by oral administration, the steps which comprise charging a cation exchanger with from 10% to 100% alkali metal ions before or after it is charged with ions of iron (III), tin, lanthanum, aluminium or zirconium.

2. The method of claim 1, wherein the said alkali metal ions are sodium and the said metal ions which react with phosphate ions are iron III ions.

3. A phosphate sorbent for oral administration capable of controlling the phosphate level in blood comprising an organic cation exchanger charged with ferric ions in a pharmaceutically acceptable carrier.

4. A phosphate sorbent according to claim 3 comprising a weakly acid organic cation exchanger.

5. The phosphate sorbent of claim 4 wherein the cation exchanger contains carboxylic acid groups, phosphonic acid groups or amidoxime groups.

6. The phosphate sorbent of claim 5 wherein the cation exchanger contains aminocarboxylic acid or iminodicarboxylic acid groups.

7. The phosphate sorbent of claim 5 wherein the cation exchanger contains aminoacetic acid or iminodiacetic acid groups.

8. The phosphate sorbent of claim 3 wherein the cation exchanger is a strongly acid cation exchanger.

9. The phosphate sorbent of claim 3 wherein the cation exchanger has a high degree of cross-linking.

10. The phosphate sorbent of claim 8 wherein the cation exchanger contains sulphonic acid groups.

11. The phosphate sorbent of claim 3 wherein the cation exchanger has a matrix comprising a polymer or a polycondensation product of an aromatic compound, an acryl, a methacryl or a vinyl compound.

12. The phosphate sorbent of claim 3 wherein the cation exchanger has a macroporous matrix.

13. The phosphate sorbent of claim 3 wherein the cation exchanger contains alkali metal ions.

14. The phosphate sorbent of claim 13 wherein the alkali metal ions are sodium ions.

15. The phosphate sorbent of claim 13 wherein the cation exchanger contains calcium or magnesium ions and the alkali metal ions.

16. The phosphate sorbent of claim 3 wherein the pharmaceutically acceptable carrier is a capsule having a cationic semipermeable wall.

* * * * *